United States Patent
Laufer

Patent Number: 5,957,919
Date of Patent: Sep. 28, 1999

[54] BLEB REDUCER

[76] Inventor: Michael D. Laufer, 1259 El Camino Real, #211, Menlo Park, Calif. 94025

[21] Appl. No.: 08/887,206

[22] Filed: Jul. 2, 1997

[51] Int. Cl.⁶ .................................................. A61B 17/38
[52] U.S. Cl. .............................................. 606/28; 606/27
[58] Field of Search ................................. 606/28, 14, 13, 606/40, 41, 42, 46, 48, 49, 27; 607/96, 98, 99, 100, 102, 122, 126, 128; 128/397

[56] References Cited

U.S. PATENT DOCUMENTS

| | | | |
|---|---|---|---|
| 3,906,955 | 9/1975 | Roberts | 606/49 |
| 3,929,137 | 12/1975 | Gonser | 606/49 |
| 4,672,969 | 6/1987 | Dew | 128/397 |
| 4,709,698 | 12/1987 | Johnston et al. | |
| 4,955,377 | 9/1990 | Lennox et al. | |
| 5,071,222 | 12/1991 | Laakmann et al. | 606/28 |
| 5,084,045 | 1/1992 | Helenowski | 606/49 |
| 5,103,804 | 4/1992 | Abele et al. | |
| 5,191,883 | 3/1993 | Lennox et al. | |
| 5,254,117 | 10/1993 | Rigby et al. | 606/42 |
| 5,368,591 | 11/1994 | Lennox et al. | |
| 5,496,311 | 3/1996 | Abele et al. | |
| 5,507,743 | 4/1996 | Edwards et al. | 606/48 |
| 5,536,267 | 7/1996 | Edwards et al. | 606/48 |
| 5,545,193 | 8/1996 | Fleischman et al. | |
| 5,586,982 | 12/1996 | Abela | 606/14 |
| 5,709,675 | 1/1998 | Williams | 606/41 |

*Primary Examiner*—Michael Buiz
*Assistant Examiner*—Julian W. Woo
*Attorney, Agent, or Firm*—Burns, Doane, Swecker & Mathis, LLP

[57] ABSTRACT

A device and method for treating hollow, elastic body structures such as blebs in lungs are provided. The device includes an elongated member having a heating element that comprises one or more energy delivery members. The method includes heating said body structure to cause at least a portion of the cross links of the collagen in the wall to unlink/open and subsequently form new cross links after the diameter of said body structure has been significantly reduced and collagen fibers have realigned.

58 Claims, 2 Drawing Sheets

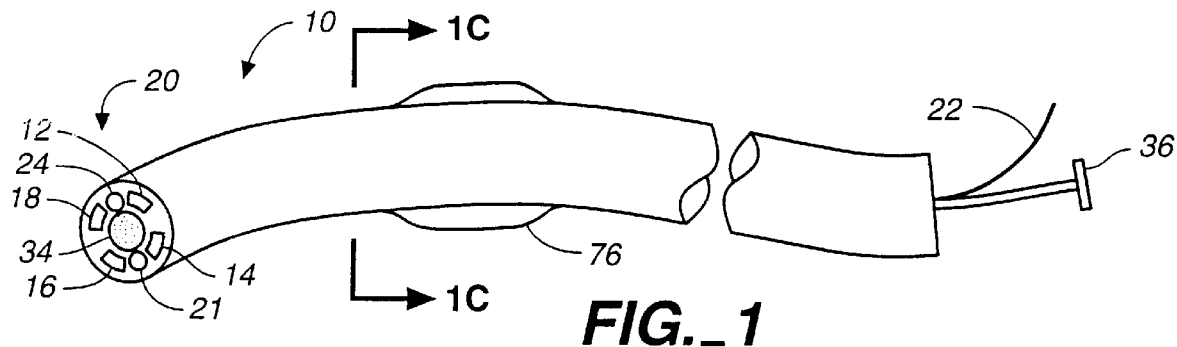
FIG._1
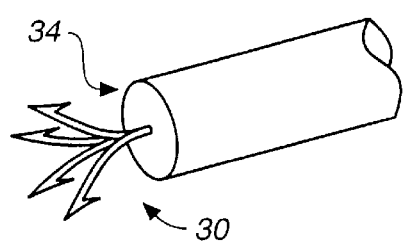
FIG._1A
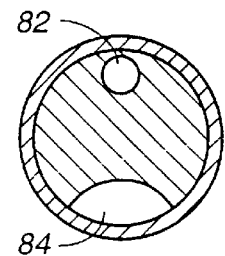
FIG._1C
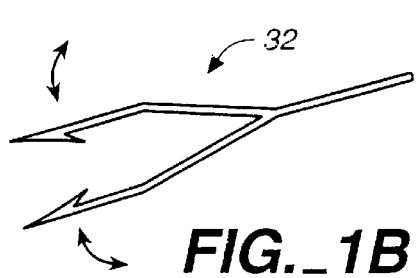
FIG._1B
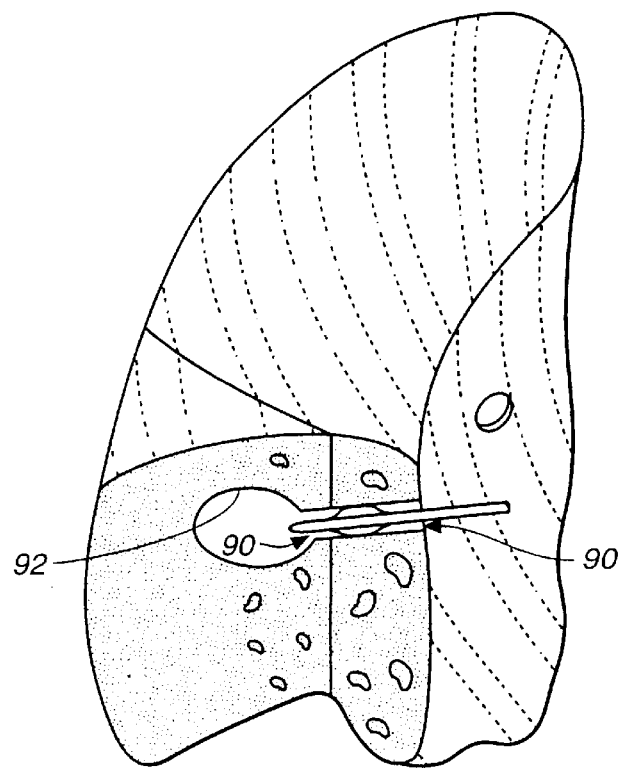
FIG._2

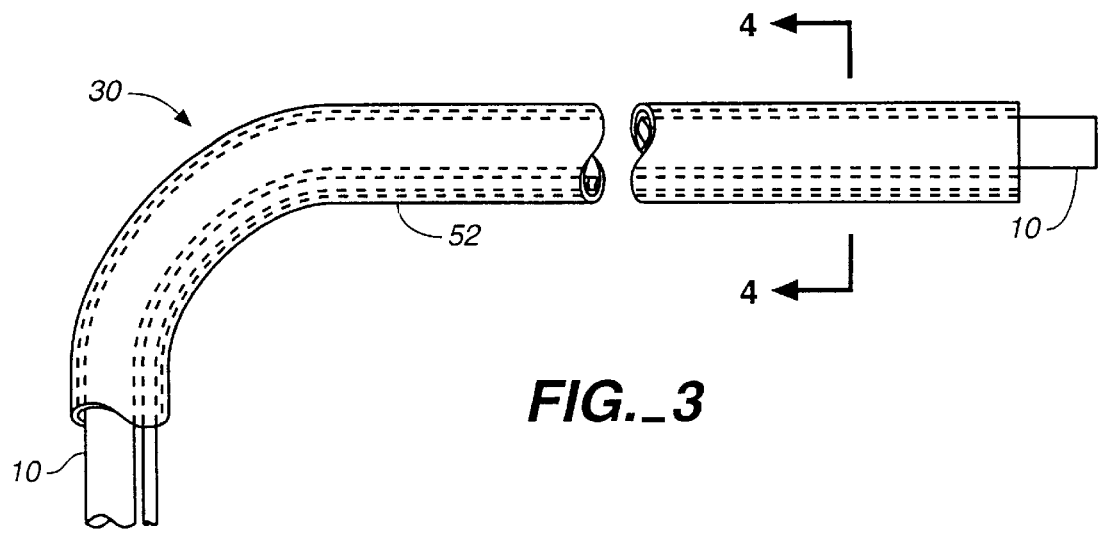
FIG._3
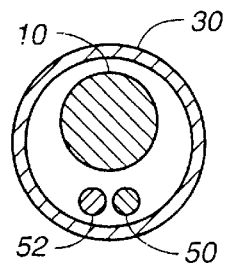
FIG._4
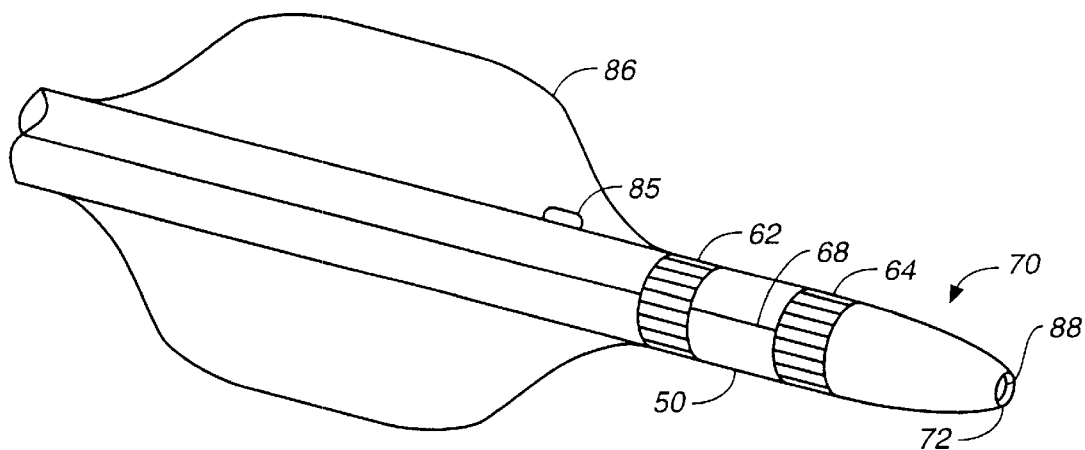
FIG._5 ns.

BLEB REDUCER

FIELD OF THE INVENTION

The present invention relates to a device and method for treatment of hollow, elastic body structures and more particularly for treatment of blebs in the lungs.

BACKGROUND OF THE INVENTION

Blebs are abnormal vacuoles in the lungs which may range from about 3 mm to several centimeters in size. Blebs often develop when alveolar walls deteriorate thereby transforming a mass of individual alveoli into one or more blebs. The alveoli are small, polyhedral recesses composed of a fibrillated connective tissue and surrounded by a few involuntary muscular and elastic fibers. As is apparent, the presence of blebs adversely affects the respiratory function of the lungs by inducing the surface area available for actual gaseous exchange in respiration. For severe cases, surgeons have endeavored to alleviate the disabling conditions associated with blebs by removing portions of lungs containing blebs. These operations are quite risky and are considered final options.

Notwithstanding the conventional treatments available, there exists a need in the art for an effective treatment for conditions associated with blebs and other hollow, elastic body structures. Specifically, there is a need for effective treatment which only requires minimal surgery.

SUMMARY OF THE INVENTION

The present invention is based in part on the discovery that the size of a bleb can be significantly reduced by subjecting the surface of the bleb to a sufficient amount of heat to cause at least a portion of the crosslinks of the collagen fibers to open and subsequently form new cross links after the collagen fibers have realigned.

In one aspect, the invention is directed to an apparatus for treating hollow, elastic body structures such as blebs in the lungs which includes a treatment device comprising an elongated member and a heating element that comprises one or more energy delivery members which when energized causes collagen in the wall of said structure to undergo a structural transformation effective to reduce the size of said structure, a means for attaching the treatment device to a surface of said structure, and a source of energy that is conducted to the heating element.

In another aspect, the invention is directed to an apparatus for treating a bleb which defines a cavity which includes a treatment device comprising an elongated member and a heating element that comprises one or more energy delivery members which when energized causes collagen in the wall of a bronchiole that is in communication with the bleb to undergo a structural transformation effective to reduce the size and to seal the bronchiole lumen, a source of energy that is conducted to the heating element, and means for removing air from the cavity.

The invention is further directed to methods of treating and removing hollow, elastic body structure such as a bleb. One method includes the procedure of heating the wall of said structure with sufficient energy to cause the collagen in the wall to undergo a structural transformation which effectively reduces the size of said structure. Another method includes the procedure of removing air from the cavity of said structure to reduce the size of the cavity. This procedure effectively reduces the size of said structure. Furthermore, the method may include heating and sealing the air passage (s) or channel(s) leading to the cavity and thereby fix the size of a bleb. In one application the bronchiole leading to the bleb is heated to seal the bronchiole lumen thereby preventing the bleb from redeveloping.

BRIEF DESCRIPTION OF THE DRAWINGS

As used herein, like reference numerals will designate similar elements in the various embodiments of the present invention wherein:

FIGS. 1, 1A, 1B and 1C illustrate an embodiment of the treatment apparatus;

FIG. 2 illustrates implementation of the treatment apparatus through a partially exposed and enlarged section of lung tissue;

FIGS. 3 and 4 illustrate a bronchoscope; and

FIG. 5 illustrates an embodiment of the treatment apparatus.

DETAILED DESCRIPTION OF THE PREFERRED EMBODIMENTS

The present invention is directed to devices and methods for treating hollow, elastic body structures that are typically abnormal manifestations. These structures have cavities whose walls contain collagen. As further described herein the collagen will respond to heat treatment thereby reducing the size of the cavities. Prior to treatment, these cavities may range from about 3 mm to several centimeters in size. The invention is particularly suited for treating blebs in the lungs. The invention will be described using the treatment of blebs as the illustrative example, however, it is understood that the invention is applicable generally to the treatment of hollow, elastic body structures.

FIG. 1 illustrates an embodiment of the inventive treatment apparatus which includes an elongated, cylindrical member 10 having a heating element that has a plurality of electrodes designated 12, 14, 16 and 18, each having an exposed distal end which may be substantially flush with the surface of the distal end 20 of the member. The electrodes are electrically connected to a source of RF energy via connector 22. Preferably the exposed surface of the electrodes collectively has a surface area of about 10 mm$^2$ to about 100 cm$^2$. The treatment apparatus has an outer diameter that is small enough to enter a bleb or can be expanded to fill the bleb or can be expanded to fill the bleb as further described herein. Typically, the outer diameter ranges from about 2 French to about 8 French prior to any expansion.

The function of the heating element is to apply a sufficient amount of energy to the walls of a bleb to cause collagen to undergo a structural transformation to cause the walls to shrink. In this embodiment, energy emanates from the exposed distal ends from the electrodes so that following treatment with this particular apparatus, the size of the bleb is significantly reduced or the bleb is eliminated altogether. As is apparent, the number and surface area of each electrode are not critical. In the case where the surface area is small relative to the diameter of the bleb, it may be necessary to move the apparatus and heat more than one area of the wall in order to transform sufficient amounts of the collagen to reduce the size of the bleb and to distribute the heat more uniformly.

The heating element is made of any suitable biocompatible material such as, for example, conductive polymer, stainless steel, platinum, other nobel metals, or shape memory alloy, such as nickel-titanium-alloy (Nitinol™ commercially available from Raychem Corporation, Menlo Park, Calif.). Member 10 is made of a flexible material so that it can be maneuvered through a catheter or bronchoscope as described herein. The term "catheter" refers generally to a tubular device suitable for insertion into the a bleb through the bronchioles. A bronchoscope is a modified catheter which is an illuminating instrument for inspecting and passing instruments (e.g., treatment device) into the bronchioles.

When the treatment apparatus is positioned at the treatment site, an RF generator is activated to provide suitable RF energy, preferably at a selected frequency in the range of 10 MHz to 1000 MHz. The emitted energy is converted within the tissue into heat in the range of about 40° C. to about 95° C. As the temperature increases, it is believed that the collagen undergoes a structural transformation whereby the collagen fibers contract and new cross links are formed.

RF energy is no longer applied after there has been sufficient transformation, e.g., shrinkage, of the collagen fibers which may be gauged by removing the heating device from the treatment site and conducting a visual inspection. Sufficient shrinkage may also be detected by fluoroscopy, external ultrasound scanning, pulse-echo ultrasound scanning, sensing the collapsing or straightening of the heating element with appropriate feedback variables, impedance monitoring or any other suitable method for pulmonary function testing.

Substantial transformation may be achieved very rapidly, depending upon the specific treatment conditions. Because the transformation can proceed at a rather rapid rate, the RF energy should be applied at low power levels. Preferably, the RF energy is applied for a length of time in the range of about 1 second to about 120 seconds. Suitable RF power sources are commercially available and well known to those skilled in the art. In one embodiment the RF generator employed has a single channel, delivering approximately 1 to 10 watts of RF energy and possessing continuous flow capability. The rate of transformation can be controlled by varying the energy delivered to the heating element.

Besides using RF energy for energizing the heating element, it is to be understood that other forms of energy such as alternating current, microwaves, ultrasound, and light either coherent (e.g., laser) or incoherent (e.g., light emitting diode or tungsten filament) can be used, and that the thermal energy generated from a resistive coil, a hot fluid element (e.g., circulating liquids, gases, combinations of liquids and gases, etc.), a curie point element, or similar elements can be used as well. The hot fluid element may comprise, for example, an elongated member similar to the one illustrated in FIG. 1 that includes a conduit system whereby heated fluid is transported through the member and then channeled outward toward the surface of the distal end 20 of the member. Regardless of the source, the energy delivered to the bleb wall should not ablate the tissue.

The heating element, as shown in FIG. 1, operates as a unipolar, internal electrode in the patient's body. An outer electrode (not shown) having a much larger surface area than that of the electrode bands is placed on the outer surface of the patient's body. For example, an external metal mesh or solid plate is placed on the skin. Both electrodes are connected to an RF generator which produces an electric field at a high frequency within the patient's body. Because the collective surface area of the electrode bands is much smaller than that of the outer electrode, the density of the high frequency electric field is much higher around the electrode bands. The electric field reaches its highest density between the two electrodes in the region near the heating element. The increased density of the field around the distal ends of the electrodes produces localized heating of the tissue of the bleb wall.

A heating element comprising a bipolar electrode can also be used. Referring to FIG. 1, in such a bipolar electrode arrangement, electrodes 12 and 16 can be connected to the positive electrode of the RF generator and electrodes 14 and 18 are connected to the negative electrode. The material between the conductive elements are electrically insulated. In this case, FIG. 1 illustrates a heating element having multiple, i.e., double, bipolar electrodes. The electrodes emit RF energy with the first conductive element acting as the active electrode and the second conductive element acting as the return electrode, or vice versa.

The treatment apparatus preferably includes a device for attaching the apparatus to the bleb wall. FIG. 1A illustrates one device which comprises a plurality of generally axially extending hooks 30 that are made of metal or other suitable material. FIG. 1B illustrates another device which comprises expandable prongs 32. The hook and prong devices are sized to be received with lumen 24 of the treatment apparatus.

The treatment apparatus can be maneuvered to a particular bleb initially through the bronchus, which upon entering the substance of the lung, divides and subdivides bipinnately, throughout the entire organ. Sometimes multiple branches arise together, and occasionally small lateral branches are given off from the sides of a main trunk. Each of the smaller subdivisions of the bronchi enters a pulmonary lobule, and is termed a lobular bronchial tube or bronchiole. The bronchiole becomes enlarged, and is termed the atrium or alveolar passage; from it are given off, on all sides, ramifications, called infundibula, which are closely beset in all directions by alveoli.

In operation, after the treatment apparatus is maneuvered to the bleb surface through the bronchiole, the hooks or prongs are projected from lumen 24 when the surgeon engages (e.g., presses) actuator 36 which is connected to the hooks or prongs via a stiff wire. The hooks or prongs are then manipulated to fasten onto tissue on the bleb surface whereupon the actuator is disengaged and the hooks or prongs are retracted. In this fashion, the bleb tissue becomes attached to the treatment apparatus and as a corollary the heating element becomes positioned adjacent to (or is in physical contact with) the bleb surface.

The treatment apparatus may further include an inflatable balloon device 76 which is made of a flexible, expandable material. As shown in FIG. 1C, the apparatus includes at least two internal passageways 82 and 84. For example, passageway 82 may be in communication with lumen 24 and passageway 84 may be in communication with the balloon device.

In operation, as illustrated in FIG. 2, after the treatment apparatus is inserted into the bronchiole 90 which leads to bleb 92, the balloon device is inflated with air or other suitable fluid so that the outer surface of the balloon is in physical contact with the inner surface of the bronchiole. Next the air is withdrawn from the bleb through lumen 24 and via passageway 84 which in turn is connected to an aspirator device (not shown). The suction will cause the size of the bleb to decrease. Once the size of the bleb has been reduced sufficiently so as to be in contact with the distal ends of the electrodes, the heating elements can be energized to complete the treatment process. The treatment apparatus may include a conventional pressure sensing gauge 21 to measure the pressure in the cavity of the bleb.

The segment of the treatment apparatus forming the balloon is fabricated of material that is expandable and substantially impervious to air or other suitable gases. In this fashion, this section of the elongated member is radially expandable and deformable in response to compressed gas or any other suitable force or material that is applied into the interior region of the elongated member. Moreover, the elongated member will substantially return to its original, non-expanded form when the internal force is deactivated or the material is withdrawn.

FIGS. 3 and 4 illustrate a bronchoscope 30 having treatment apparatus 10 slidably positioned within a lumen. The device also includes an image-transmitting fiber 50 and illuminating fiber 52. Any conventional bronchoscope with an appropriately sized and directed working lumen may be employed. The image transmitting fiber collects light from the distal end of the treating apparatus and directs the light to a viewing apparatus (not shown) for displaying an image of the obstructed air passage. The bronchoscope may have a panning system which enables the tips to be moved in different directions.

When treating a particular site, excessive fluid is first removed from the bleb by conventional means such as with a suction catheter. Thereafter, the bronchoscope can be advanced from the person's nasal or oral cavity, and through the trachea, main stem bronchus, and into a bleb. The heat treatment device is connected to an RF generator which could be located in the handle of the device or located remotely from the patient.

The treatment device is advanced forward from the bronchoscope before the attachment means (e.g., hook or prong device) is actuated. Thereafter, the RF generator is energized. Depending on the number of, and/or surface area of, the electrodes, the treatment device can be moved to another position for further heat treatment. After completion of the treatment, RF energy to the electrodes is discontinued, the attachment means released, and the bronchoscope is then removed from the patient.

The heating apparatus can be made to provide protection against overheating of the connective tissue which may cause the collagen to denature. Temperature monitoring and impedance monitoring can be utilized in a system which provides feedback to the user in the form of sounds, lights, other displays or which shuts down the application of energy from the heating element to the treatment site when sufficient transformation is detected and to avoid burning of the treatment site. The amount of energy applied can be decreased or eliminated manually or automatically under certain conditions. For example, the temperature of the wall of the air passage, or of the heating element can be monitored and the energy being applied adjusted accordingly. The surgeon can, if desired, override the feedback control system. A microprocessor can be included and incorporated into the feedback control system to switch the power on and off, as well as modulate the power. The microprocessor can serve as a controller to monitor the temperature and modulate the power. Similarly, the treatment device can provide feedback protection against excessive suction of the cavity and/or excessive inflation of the balloon.

FIG. 5 illustrates an embodiment of another inventive treatment apparatus which includes an elongated, cylindrical member 50 having a heating element that has a plurality of electrodes designated 62 and 64 located on the outer surface of the member. The electrodes are electrically connected to a source of RF energy via connector 68. Preferably each electrode is configured as a band as shown that has a width of about 0.5 mm to about 3 mm and preferably each electrode band is separated from the next by a distance of about 1 mm to 5 mm. It is understood that the heating element comprises one or more electrode bands. The apparatus has a distal end 70 that is parabolically-shaped to reduce the amount of resistance encountered when the apparatus is advanced into the air passages. The distal end includes lumen 72 which can accommodate attachment devices shown in FIGS. 1A and 1B. The apparatus further includes a balloon device 86 which is depicted in the inflated position.

The apparatus has an outer diameter that is approximately equal to (or can be expandable to equal) the desired final inner diameter of a bronchiole that leads to a bleb to be treated. Typically, the outer diameter ranges from about 2 French to about 6 French.

The function of the treating element is to apply a sufficient amount of energy to the walls of a bronchiole to cause collagen in the walls to undergo a structural transformation to seal the lumen. As is apparent, the number and width of each electrode band are not critical. In the case where there is only one electrode band, it may be necessary to move the apparatus and heat more than one area of the lumen wall in order to transform sufficient amounts of the collagen. Member 50 is also preferably made of a flexible material so that it can be maneuvered through a catheter or bronchoscope as described herein.

The treatment apparatus can be inserted into a bronchiole which leads to the cavity of the bleb. Thereafter, the balloon device is inflated with air or other suitable fluid so that the outer surface of the balloon is in physical contact with the inner surface of the bronchiole. A conventional pressure gauge 85 may be incorporated which can be employed as a feedback mechanism to avoid overinflation, for example. Next the air is withdrawn from the bleb through lumen 72 which is connected to an aspirator device (not shown). The aspirator will create sufficient suction to cause collapse of the bleb wall and ultimately reduce the size of the bleb cavity.

When the suction is applied, tissue forming the bleb wall is drawn toward lumen 72 and eventually the bleb becomes invaginated or turned inside out as tissue enters inside the lumen. To facilitate the heating of this tissue, in one embodiment, the apparatus shown in FIG. 5, electrode 88 is positioned in the inside surface of lumen 72. In this fashion, as bleb tissue is pulled into the lumen by the suction, the invaginated bleb can be heat sealed by electrode 88. Alternatively, the electrodes can be positioned at the tip of the apparatus for heating the bronchiole that leads to the bleb or to seal the bronchiole to the invaginated bleb. Either way, the balloon remains inflated during the heat treatment process to maintain the vacuum. To facilitate this procedure, electrode bands can be positioned near the distal portion 70 of the treatment apparatus. Moreover, the distal portion can be tapered so that treatment apparatus can be gradually withdrawn from the bronchiole lumen as its diameter decreases.

When the treatment apparatus is positioned at the treatment site, an RF generator is activated to provide suitable RF energy, preferably at a selected frequency in the range of 10 MHz to 1000 MHz. The emitted energy is converted within the tissue into heat in the range of about 40° C. to about 95° C. RF energy is no longer applied after there has been sufficient transformation, e.g., shrinkage, of the collagen fibers which may be gauged by removing the heating device from the treatment site and visually determining whether the lumen remains uncollapsed. Sufficient shrinkage may also be detected by fluoroscopy, external ultrasound scanning, pulse-echo ultrasound scanning, sensing the collapsing or straightening of the heating element with appropriate feedback variables, impedance monitoring or any other suitable method.

Besides using RF energy for energizing the heating element, it is to be understood that other forms of energy such as those described for the device of FIG. 1 including alternating current, microwaves, ultrasound, and light either coherent (e.g., laser) or incoherent (e.g., light emitting diode or tungsten filament) can be used, and that the thermal energy generated from a resistive coil, a hot fluid element (e.g., circulating liquids, gases, combinations of liquids and gases, etc.) can be used as well.

The heating element, as shown in FIG. 5 operates as a unipolar, internal electrode in the patient's body. An outer electrode (not shown) having a much larger surface area than that of the electrode bands is placed on the outer surface of the patient's body. A heating element comprising a bipolar electrode can also be used.

While the heating elements have been shown as electrode bands, other configurations can be used such as, for example, spiral, ring and grid patterns. These elements will create corresponding patterns on the lumen wall. One limitation is that the heating elements have sufficient surface area in contact with the wall of the lumen so that the heat treatment process can be completed within a reasonable time.

The invention is also directed to the demonstration or instruction of the inventive surgical techniques including, but not limited to, actual instructions involving patients, audio-visual presentations, animal demonstrations, and the like.

While several particular embodiments of the invention have been illustrated and described, it will be apparent that various modifications can be made without departing from the spirit and scope of the invention. Accordingly, it is not intended that the invention be limited, except as by the appended claims.

What is claimed is:

1. An apparatus for treating an elastic body structure that defines a cavity which comprises:
    a treatment device comprising an elongated member and a non-tissue penetrating heating element that comprises one or more energy delivery members which when energized causes tissue in the wall of the cavity to undergo a structural transformation effective to reduce the size of the cavity;
    non-energy delivering means for attaching the treatment device to a surface of the cavity with the non-tissue penetrating heat element abutting walls of the cavity; and
    a source of energy that is conducted to the heating element.

2. The apparatus of claim 1 wherein the source of energy produces energy in a form that is selected from the group consisting of RF energy, alternating current, microwaves, ultrasound, coherent light, incoherent light, thermal energy, and mixtures thereof.

3. The apparatus of claim 2 wherein the one or more energy delivery members each comprise an electrode and wherein a segment of the elongated member comprises elastic material and wherein each electrode has a distal portion that is positioned on an outer surface of the segment.

4. An apparatus for treating an elastic body structure that defines a cavity which comprises:
    a treatment device comprising an elongated member and a heating element that comprises one or more energy delivery members which when energized causes tissue in the wall of the cavity to undergo a structural transformation effective to reduce the size of the cavity;
    means for attaching the treatment device to a surface of the cavity; and
    a source of energy that is conducted to the heating element, wherein the one or more energy delivery members comprise one or more sets of double electrode bands wherein each set comprises a first electrode which is connected to the positive electrode of an RF generator and a second electrode which is connected to the negative electrode of the RF generator.

5. The apparatus of claim 1 wherein the one or more energy delivery members emit light energy.

6. The apparatus of claim 1 wherein the one or more energy delivery members comprise a conduit that channels heated fluid into and out of the elongated member.

7. The apparatus of claim 1 wherein the source of energy comprises a radio frequency generator.

8. The apparatus of claim 1 further comprising a feedback indicator.

9. The apparatus of claim 8 wherein the feedback indicator is an auditory signal.

10. The apparatus of claim 8 wherein the feedback indicator is a visual signal.

11. The apparatus of claim 8 wherein the feedback indicator is indicative of tissue shrinkage.

12. The apparatus of claim 8 wherein the feedback indicator is indicative of temperature.

13. The apparatus of claim 8 wherein the feedback indicator is indicative of electrical characteristics.

14. The apparatus of claim 8 wherein the feedback indicator is indicative of pressure within the cavity.

15. The apparatus of claim 1 wherein the means for attaching the treatment device comprises hooks or prongs.

16. The apparatus of claim 1 wherein the treatment device has a tubular member on an outer surface of the elongated member and wherein the elongated member defines a first diameter and the tubular member having a second, expanded and deformed diameter upon an application of a radially, outwardly extending force.

17. The apparatus of claim 1 wherein the heating elements further comprise one or more electrode bands that are each spaced apart from an adjacent band.

18. The apparatus of claim 1 wherein the treatment device comprises means for removing air from the cavity.

19. The apparatus of claim 18 wherein the means for removing air comprises a lumen in the treatment device that is in communication with an aspirator.

20. An apparatus for treating an elastic body structure that defines a cavity which comprises:
    a treatment device comprising an elongated member and a heating element that comprises one or more energy delivery members which when energized causes tissue in the wall of the cavity to undergo a structural transformation effective to reduce the size of the cavity;
    means for attaching the treatment device to a surface of the cavity; and
    a source of energy that is conducted to the heating element wherein the treatment device includes a lumen for removing air from the cavity and the heating element is located on an inner surface of the lumen.

21. An apparatus for treating a bleb which comprises:
    a treatment device comprising an elongated member and a heating element that comprises one or more energy delivery members which when energized causes tissue in the wall of a bronchiole that is in communication with the bleb to undergo a structural transformation effective to reduce the size and to seal the bronchiole lumen;

a source of energy that is conducted to the heating element;

an inflatable balloon positioned on the elongated member for sealing the bronchiole and preventing air from passing into the bleb; and means for removing air from the bleb.

22. The apparatus of claim 21 wherein the one or more energy delivery members each comprises an electrode band.

23. The apparatus of claim 22 wherein each electrode is positioned on an outer surface of the inflatable balloon.

24. The apparatus of claim 21 wherein the one or more energy delivery members comprise one or more sets of double electrode bands wherein each set comprises a first electrode which is connected to the positive electrode of an RF generator and a second electrode which is connected to the negative electrode of the RF generator.

25. An apparatus for treating a bleb which defines a cavity which comprises:

a treatment device comprising an elongated member and a heating element that comprises one or more energy delivery members which when energized causes tissue in the wall of a bronchiole that is in communication with the bleb to undergo a structural transformation effective to reduce the size and to seal the bronchiole lumen;

a source of energy that is conducted to the heating element;

means for removing air from the cavity; and wherein the one or more energy delivery members emit light energy.

26. An apparatus for treating a bleb which defines a cavity which comprises:

a treatment device comprising an elongated member and a heating element that comprises one or more energy delivery members which when energized causes tissue in the wall of a bronchiole that is in communication with the bleb to undergo a structural transformation effective to reduce the size and to seal the bronchiole lumen;

a source of energy that is conducted to the heating element;

means for removing air from the cavity; and wherein the one or more energy delivery members comprise a conduit that channels heated fluid into and out of the elongated member.

27. The apparatus of claim 21 wherein the source of energy comprises a radio frequency generator.

28. The apparatus of claim 21 further comprising a feedback indicator.

29. The apparatus of claim 28 wherein the feedback indicator is an auditory signal.

30. The apparatus of claim 28 wherein the feedback indicator is a visual signal.

31. The apparatus of claim 28 wherein the feedback indicator is indicative of shrinkage.

32. The apparatus of claim 28 wherein the feedback indicator is indicative of temperature.

33. The apparatus of claim 28 wherein the feedback indicator is indicative of electrical characteristics.

34. The apparatus of claim 21 further comprising means for attaching the treatment device to the bleb comprising hooks or prongs.

35. An apparatus for treating a bleb which defines a cavity which comprises:

a treatment device comprising an elongated member and a heating element that comprises one or more energy delivery members which when energized causes tissue in the wall of a bronchiole that is in communication with the bleb to undergo a structural transformation effective to reduce the size and to seal the bronchiole lumen;

a source of energy that is conducted to the heating element;

means for removing air from the cavity; and wherein the treatment device has a tubular member on an outer surface of the elongated member wherein the elongated member defines a first diameter and the tubular member having a second, expanded and deformed diameter upon an application of a radially, outwardly extending force, which second diameter is variable and dependent upon the amount of force applied to the tubular member.

36. The apparatus of claim 35 wherein the means for removing air comprises a lumen in the treatment device that is in communication with aspirator.

37. The apparatus of claim 36 wherein the heating element is located on an inner surface of the lumen.

38. A method of treating a bleb in a lung that defines a cavity that comprises the step of:

heating a wall surface of said bleb to a temperature effective to cause tissue in the wall of the cavity to undergo a structural transformation to reduce the size of the cavity.

39. The method of claim 38 wherein the wall of the cavity is heated to a temperature in the range between about 40° C. and about 95° C.

40. The method of claim 39 wherein the wall is heated for about 1 to about 120 seconds.

41. The method of claim 38 wherein the step of heating the surface comprises:

advancing a treatment apparatus into said structure of the individual; and energizing the treatment apparatus to raise the temperature of the surface to sufficiently affect collagen in the wall of the cavity to undergo a structural transformation.

42. The method of claim 41 wherein the treatment apparatus comprises:

a treatment device comprising an elongated member and a heating element that comprises one or more energy delivery members which when energized causes collagen in the wall of said structure to undergo a structural transformation effective to reduce the size of the cavity;

means for attaching the treatment device to a surface of said structure; and a source of energy that is conducted to the heating element.

43. A method of treating a bleb which defines a cavity in the lung of an individual that comprises the steps of:

removing air from the cavity through a bronchiole that is in communication with the cavity to cause a reduction in size of the cavity; and heating the wall of the bronchiole to seal the bronchiole lumen.

44. The method of claim 43 wherein the wall of the bronchiole is heated to a temperature in the range between about 40° C. and about 95° C.

45. The method of claim 44 wherein the wall of the bronchiole is heated for about 1 to about 120 seconds.

46. The method of claim 43 wherein the step of heating the wall of the bronchiole comprises:

advancing a treatment apparatus into a lumen of the bronchiole;

energizing the treatment apparatus to raise the temperature of the surface of the wall to sufficiently affect collagen in the wall to undergo a structural transformation.

47. The method of claim 46 wherein the treatment apparatus comprises:

a treatment device comprising an elongated member and a heating element that comprises one or more energy delivery members which when energized causes collagen in the wall of a bronchiole that is in communication with the bleb to undergo a structural transformation effective to reduce the size and seal the bronchiole;

a source of energy that is conducted to the heating element; and means for removing air from the cavity.

48. A method of treating a bleb which defines a cavity in the lung of an individual that comprises the steps of:

drawing air from the cavity to cause a reduction in size of the cavity; and heating a surface of the bleb wall to seal the cavity.

49. The method of claim 48 wherein the step of drawing air from the cavity causes the wall of the bleb to invaginate.

50. The method of claim 49 wherein heating the surface of the bleb wall fixes the size of the bleb.

51. The method of claim 48 wherein the wall of the bleb is heated to a temperature in the range between about 40° C. and about 95° C.

52. The method of claim 51 wherein the wall of the bleb is heated for about 1 to about 120 seconds.

53. The method of claim 48 wherein the step of drawing air from the cavity comprises:

(a) advancing a treatment apparatus into a lumen of the bronchiole that is in communication with the cavity wherein the treatment apparatus comprises:

(i) an elongated member and a heating element that comprises one or more energy delivery members which when energized causes collagen in the bleb wall to undergo a structural transformation effective to reduce the size and seal the bleb;

(ii) a source of energy that is conducted to the heating element; and;

(iii) means for removing air from the cavity; and (b) activating said means for removing air.

54. The method of claim 53 wherein the means for removing air comprises a lumen in the treatment apparatus that is in communication with an aspirator.

55. The method of claim 54 wherein the heating element is located on an inner surface of the lumen.

56. An apparatus for treating an elastic body structure that defines a cavity which comprises:

a treatment device comprising an elongated member and a heating element that comprises one or more energy delivery members which when energized causes tissue in the wall of the cavity to undergo a structural transformation effective to reduce the size of the cavity;

means for attaching the treatment device to a surface of the cavity;

a source of energy that is conducted to the heating element; and wherein the heating elements further comprise one or more electrode bands that are each spaced apart from an adjacent band.

57. The apparatus of claim 1 wherein the treatment device includes a proximal end and a distal end, and the heating element is positioned proximal of the attaching means.

58. The apparatus of claim 3 wherein the elastic segment of the elongated member is radially expandable.

\* \* \* \* \*